(12) United States Patent
Jomard et al.

(10) Patent No.: US 8,669,233 B2
(45) Date of Patent: Mar. 11, 2014

(54) COMBINATION OF COMPOUNDS FOR TREATING OR PREVENTING SKIN DISEASES

(75) Inventors: André Jomard, Saint Vallier de Thiey (FR); Laurent Fredon, Roquefort les Pins (FR); Olivier Roye, Fayence (FR)

(73) Assignee: Galderma Research & Development, Biot (FR)

( * ) Notice: Subject to any disclaimer, the term of this patent is extended or adjusted under 35 U.S.C. 154(b) by 29 days.

(21) Appl. No.: 13/201,762

(22) PCT Filed: Feb. 16, 2010

(86) PCT No.: PCT/FR2010/050259
§ 371 (c)(1),
(2), (4) Date: Oct. 10, 2011

(87) PCT Pub. No.: WO2010/092312
PCT Pub. Date: Aug. 19, 2010

(65) Prior Publication Data
US 2012/0035123 A1    Feb. 9, 2012

(30) Foreign Application Priority Data
Feb. 16, 2009  (FR) ..................... 09 50981

(51) Int. Cl.
*A61K 31/70* (2006.01)
(52) U.S. Cl.
USPC ........................................ 514/30
(58) Field of Classification Search
USPC .................................. 514/30, 450
See application file for complete search history.

(56) References Cited

U.S. PATENT DOCUMENTS

| 5,952,372 | A | 9/1999 | McDaniel |
|---|---|---|---|
| 2005/0020600 | A1 | 1/2005 | Scherer |
| 2005/0165079 | A1 | 7/2005 | Shanler et al. |
| 2006/0171974 | A1 | 8/2006 | DeJovin et al. |
| 2008/0139488 | A1 | 6/2008 | Kaoukhov et al. |
| 2008/0153901 | A1 | 6/2008 | Kaoukhov et al. |
| 2008/0176928 | A1 | 7/2008 | Kaoukhov et al. |
| 2008/0194664 | A1 | 8/2008 | Kaoukhov et al. |
| 2009/0093421 | A1* | 4/2009 | Kaoukhov et al. .............. 514/30 |
| 2009/0258938 | A1 | 10/2009 | Kaoukhov et al. |
| 2009/0264516 | A1 | 10/2009 | Kaoukhov et al. |

FOREIGN PATENT DOCUMENTS

| FR | 2 901 703 A | 12/2007 |
|---|---|---|
| WO | WO 2006/097628 A1 | 9/2006 |
| WO | WO 2006/131651 A2 | 12/2006 |
| WO | WO 2006/131652 A1 | 12/2006 |
| WO | WO 2006/131653 A1 | 12/2006 |
| WO | WO 2007/054822 A2 | 5/2007 |
| WO | WO 2008/037935 A2 | 4/2008 |
| WO | WO 2008/037936 A1 | 4/2008 |

OTHER PUBLICATIONS

Asio et al., "*Mansonella perstans:* safety and efficacy of ivermectin alone, albendazole alone and the two drugs in combination", Annals of Tropical Medicine and Parasitology, Jan. 2009, pp. 31-37, vol. 103, No. 1.
International Search Report (PCT/ISA/210) issued on May 4, 2010, by European Patent Office as the International Searching Authority for International Application No. PCT/FR2010/050259.
Young et al., "Tachyphylaxis in 12-0-Tetradecanoylphorbol Acetate and Arachidonic Acid-Induced Ear Edema", The Journal of Investigative Dermatology, 1983, 80, 48-52.
Young et al., "The Mouse Ear Inflammatory Response to Topical Arachidonic Acid", The Journal of Investigative Dermatology, 1984, 82, 367-371.

* cited by examiner

*Primary Examiner* — Elli Peselev
(74) *Attorney, Agent, or Firm* — Dentons US LLP

(57) ABSTRACT

A combination of compounds for treating skin diseases and particularly rosacea and ocular rosacea is described. The combination of a compound of the avermectin family or of the mylbemycin family with a compound of the family of the alpha-1 or alpha-2 adrenergic receptor agonists is also described. In addition, a product in the form of a kit including: (a) a first composition containing a compound of the avermectin family or of the mylbemycin family, and (b) a second composition different from the first one and containing a compound of the family of the alpha-1 or alpha-2 adrenergic receptor agonists, as a combination product to be used as a drug for treating and/or preventing skin diseases and particularly rosacea and ocular rosacea, wherein said first and second compositions can be applied simultaneously, separately or with a time delay is described.

10 Claims, 2 Drawing Sheets

COMBINATION OF COMPOUNDS FOR TREATING OR PREVENTING SKIN DISEASES

This application is the United States national phase of PCT/FR2010/050259, filed Feb. 16, 2010, and designating the United States (published in the French language on Aug. 19, 2010, as WO 2010/092312 A1; the title and abstract were also published in French), which claims priority under 35 U.S.C. §119 of FR 0950981, filed Feb. 16, 2009, each hereby expressly incorporated by reference in its entirety and each assigned to the assignee hereof.

The invention relates to a combination of compounds for treating skin diseases in humans, particularly rosacea and ocular rosacea.

Rosacea is a common chronic and progressive inflammatory dermatosis related to vascular relaxation. It mainly affects the central part of the face and is characterized by a reddening of the face or hot flushes, facial erythema, papules, pustules, telangiectasia and sometimes ocular lesions called ocular rosacea. In serious cases, particularly in men, the soft tissue of the nose can swell and produce a bulbous swelling called rhinophyma.

Rosacea generally occurs between the ages of 25 and 70, and it is much more common in people with a fair complexion. It affects more particularly women, although this disease is generally more severe in men. Rosacea is chronic and persists for years with periods of exacerbation and remission.

The pathogenesis of rosacea is poorly understood. Many factors may be involved without necessarily inducing this disease. They are, for example, psychological factors, gastrointestinal disorders, environmental factors (exposure to the sun, temperature, humidity), emotional factors (stress), food-related factors (alcohol, spices), hormonal factors, vascular factors, or even an infection with *Helicobacter pilori*.

Conventionally, rosacea is treated orally or topically with antibiotics such as tetracyclines, erythromycin or clindamycin, but also with vitamin A, salicylic acid, antifungal agents, steroids, metronidazole (an antibacterial agent) or with isotretinoin in severe forms or else with anti-infectives such as benzoyl peroxide or else with azelaic acid. The treatment of rosacea with ivermectin, which targets the *Demodex folliculorum* parasite present on the skin of patients, is also known (U.S. Pat. No. 5,952,372). The treatment of rosacea with alpha-1 or alpha-2 adrenergic receptor agonists is also known (US 2006/0171974A1, US 2005/0165079A1, US 2005/0020600A1).

These treatments have side effects that are unpleasant for the patient, such as irritation or intolerance phenomena. In addition, none of the existing treatments make it possible to effectively treat and/or prevent all the symptoms associated with rosacea.

Taking into account the aforementioned, there is therefore a need to produce a more effective treatment for rosacea, which does not have the side effects observed in the prior art. There is in particular a need to produce a composition which confers a greater tolerance of the active ingredients, while at the same time reducing their side effects.

Surprisingly, the applicant has observed that a combination of a compound of the avermectin family or of the milbemycin family with a compound of the alpha-1 or alpha-2 adrenergic receptor agonist family allows a more effective treatment of rosacea, with fewer side effects irrespective of the duration of application of this combination. In particular, such a combination makes it possible to substantially reduce the duration of treatment and to obtain a greater reduction in the symptoms of rosacea. This combination may also make it possible to eliminate the rebound effect normally observed at the end of treatment with alpha-1 or alpha-2 adrenergic receptor agonists.

A subject of the invention is a combination of a compound of the avermectin family or of the milbemycin family with a compound of the alpha-1 or alpha-2 adrenergic receptor agonist family, for application thereof as a medicament for treating and/or preventing skin diseases and particularly rosacea and ocular rosacea.

A subject of the invention is also the use of a combination of a compound of the avermectin family or of the milbemycin family with a compound of the alpha-1 or alpha-2 adrenergic receptor agonist family for the production of a medicament intended for treating and/or preventing skin diseases and particularly rosacea and ocular rosacea.

A subject of the present invention is also a pharmaceutical, in particular dermatological, composition comprising, in a physiologically acceptable medium, at least one compound of the avermectin family or of the milbemycin family and at least one compound of the alpha-1 or alpha-2 adrenergic receptor agonist family, intended for treating and/or preventing skin diseases and particularly rosacea and ocular rosacea.

The term "dermatological composition" is intended to mean a pharmaceutical composition applied to the skin. The term "physiologically acceptable medium" is intended to mean a medium that is compatible with the skin, the mucous membranes and/or the skin appendages.

The term "skin diseases" is intended to mean cutaneous and ocular disorders. By way of nonlimiting example, mention may be made of acne, hyperseborrhea, rosacea, ocular rosacea, psoriasis and atopic dermatitis. The skin infection is more particularly rosacea or ocular rosacea.

A subject of the invention is also the use of such a composition for the production of a medicament intended for preventing and/or treating skin diseases and particularly rosacea and ocular rosacea.

A subject of the invention is also a product in the form of a kit compressing:

(a) a first composition comprising a compound of the avermectin family or of the milbemycin family, and (b) a second composition different from the first one and comprising a compound of the alpha-1 or alpha-2 adrenergic receptor agonist family, as a combination product for application thereof as a medicament for treating and/or preventing skin diseases and particularly rosacea and ocular rosacea, wherein said first and second compositions can be applied simultaneously, separately or with a time delay.

A subject of the invention is also the use of a product in the form of a kit containing:

(a) a first composition comprising a compound of the avermectin family or of the milbemycin family, and (b) a second composition different from the first one and comprising a compound of the alpha-1 or alpha-2 adrenergic receptor agonist family, as a combination product for the production of a medicament intended for treating and/or preventing skin diseases and particularly rosacea and ocular rosacea, wherein said first and second compositions can be applied simultaneously, separately or with a time delay.

Figure 1:
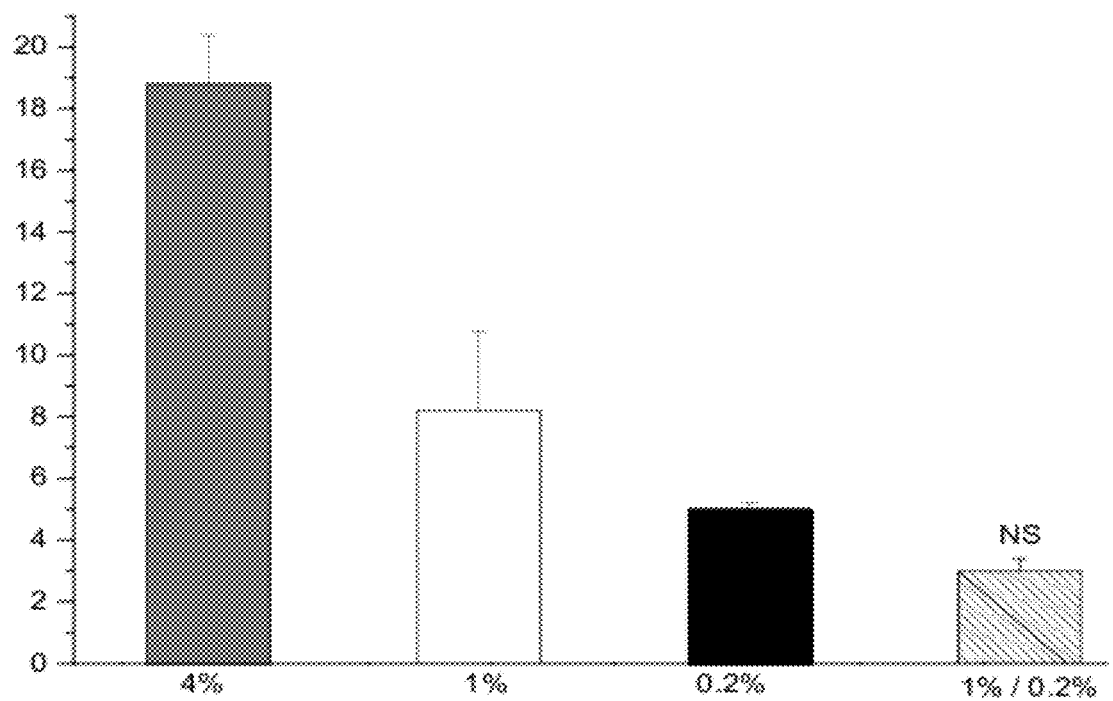
FIG. 1 is a bar graph of the average measurement of the thickness of the mouse ear after various treatments as detailed later herein, subtracted from control, as a measure of anti-inflammatory effect.

According to the invention, the compound of the avermectin family is advantageously chosen from ivermectin, invermectin, avermectin, abamectin, doramectin, eprinomectin and selamectin, aversectin B, AB or C, emamectin B1 a, emamectin B1b and their derivatives, or latidectin. The compound of the avermectin family is preferably ivermectin.

According to the invention, the compound of the milbemycin family is advantageously chosen from lepimectin, milbemectin, milbemycin oxime, moxidectin, 6'-ethyllepimectin, 6'-methyllepimectin and its derivatives or nemadectin α, β, γ or δ.

According to the invention, the compound of the alpha-1 adrenergic receptor agonist family is advantageously chosen from metaraminol bitartrate, midodrine, methoxamine, mephentermine, phenylephrine, oxymetazoline, tetrahydrozoline, naphazoline or xylometazoline, or their salts.

More particularly, the compound of the alpha-1 adrenergic receptor agonist family, as defined above, is in hydrochloride or bitartrate form.

According to the invention, the compound of the alpha-2 adrenergic receptor agonist family is advantageously chosen from apraclonidine, brimonidine, clonidine, mirtazapine, dexmedetomidine, guanbenz acetate, lidamidine, lofexidine, methyldopa, rilmenidine, talipexole, tiamenidine, tizanidine, tolonidine or their salts.

More particularly, the compound of the alpha-2 adrenergic receptor agonist family, as defined above, is in tartrate form.

More particularly, the compound of the alpha-2 adrenergic receptor agonist family may be brimonidine or its tartaric salt.

The combination according to the invention more particularly contains a compound of the avermectin family and a compound of the alpha-2 adrenergic receptor agonist family.

Preferentially, the combination according to the invention contains brimonidine and ivermectin.

In the context of the present invention, a combination of a compound of the avermectin family or of the milbemycin family with a compound of the alpha-1 or alpha-2 adrenergic receptor agonist family means that said combined compounds can be either present in the same composition, or present separately from one another in separate compositions, forming for example a product in the form of a kit. In other words, these compounds are intended to be administered to a patient in the context of the same treatment, i.e. over a common period of treatment, either at the same time, optionally being included in one and the same composition, or at different moments. Furthermore, they can be administered by identical or different administration methods and/or be included in identical or different compositions.

The combination of the abovementioned compounds present separately in separate compositions, and in particular in the case of a product in the form of a kit, makes it possible to limit the interactions of the compound(s) of the avermectin family, in particular ivermectin, or of the milbemycin family, with the compound(s) of the alpha-1 or alpha-2 adrenergic receptor agonist family. This also makes it possible to limit as much as possible the interactions of the compound(s) of the avermectin family, in particular ivermectin, or of the milbemycin family, with the numerous excipients normally contained in a single composition, and in particular the excipients contained in the composition comprising the compounds of the alpha-1 or alpha-2 adrenergic receptor agonist family. The compositions according to the invention, applied simultaneously or successively, are thus very well tolerated, precise in terms of amount of active compounds delivered, and practical to use. They also offer the patients comfort and hydration.

In the case of a combination of the abovementioned compounds present separately in separate compositions, and in particular in the case of a product in the form of a kit, a compound of the avermectin family or of the milbemycin family can first be applied to the skin of a patient, and then a compound of the alpha-1 or alpha-2 adrenergic receptor agonist family can be applied, or vice versa.

In the compositions according to the invention, the compound of the avermectin family or of the milbemycin family is present at a concentration of between 0.001 and 10% by weight, relative to the total weight of the composition comprising it, preferably between 0.01 and 5% by weight, and in particular 0.75%, 1%, 1.5% or 2%. When a composition comprises several of these compounds, their total concentration is included in the abovementioned amounts.

In the compositions according to the invention, the compound of the alpha-1 or alpha-2 adrenergic receptor agonist family is present at a concentration of between 0.01 and 20% by weight, relative to the total weight of the composition, preferably between 0.02 and 10%, particularly preferably between 0.05 and 5% by weight, relative to the total weight of the composition. When a composition comprises several of these compounds, their total concentration is included in the abovementioned amounts.

Particularly preferably, the combination comprises a compound of the avermectin family or of the milbemycin family present at a concentration of between 0.01 and 5% by weight, relative to the total weight of the composition comprising it, and a compound of the alpha-1 or alpha-2 adrenergic receptor agonist family present at a concentration of between 0.01 and 5% by weight, relative to the total weight of the composition.

Said composition according to the invention contains more particularly a compound of the avermectin family and a compound of the alpha-2 adrenergic receptor agonist family.

Preferentially, the composition according to the invention comprises brimonidine and ivermectin.

The combination according to the invention and the compositions comprising the compounds of this combination are in particular intended for topical application to the skin and/or for ocular application to the eyes.

The compositions of the invention also comprise a pharmaceutically or cosmetically acceptable vehicle, i.e. a vehicle suitable for use in contact with human cells, without toxicity, irritation, undue allergic response and the like, and proportioned at a reasonable advantage/risk ratio.

The compositions of the invention may also comprise at least one other therapeutic agent capable of increasing the efficacy of the treatment.

The compositions of the invention may also comprise any additive normally used in the pharmaceutical or dermatological field, which is compatible with the compound of the avermectin family or of the milbemycin family and/or the compound of the alpha-1 or alpha-2 adrenergic receptor agonist family that is/are present.

Mention may in particular be made of sequestering agents, antioxidants, sunscreens, preservatives, for example DL-alpha-tocopherol, fillers, electrolytes, humectants, colorants, of customary inorganic or organic bases or acids, fragrances, essential oils, cosmetic active agents, moisturizers, vitamins, essential fatty acids, sphingolipids, artificial tanning compounds such as DHA, agents for soothing and protecting the skin, such as allantoin, propenetrating agents, gelling agents, or a mixture thereof. Of course, those skilled in the art will take care to select this or these optional additional compound(s), and/or the amount thereof, in such a way that the advantageous properties of the composition according to the invention are not, or not substantially, impaired.

These additives may be present in the composition in a proportion of from 0 to 20% by weight, relative to the total weight of the composition.

The administration may be carried out topically, enterally or orally, parenterally or ocularly.

Among these routes of administration, the topical route and the ocular route are particularly preferred.

The compositions of the present invention may be in any of the galenical forms normally used for topical administration, in particular in the form of solutions, lotions, gels, emulsions of liquid or semi-liquid consistency of the milk type, obtained by dispersion of a fatty phase in an aqueous phase (O/W) or vice versa (W/O), or suspensions or emulsions of soft, semi-liquid or solid consistency, of the cream or ointment type, or else microemulsions, microcapsules, microparticles or vesicular dispersions of ionic and/or nonionic type.

Advantageously, the composition comprises an ointment, a cream, a lotion or a gel.

By way of illustration and without being in any way limiting in nature, various formulations of compositions according to the invention and also the results of a study of the anti-inflammatory activity of the combination of a compound of the avermectin family or of the milbemycin family with a compound of the alpha-1 or alpha-2 adrenergic receptor agonist family will now be given.

EXAMPLE 1

| Ingredients | % by weight relative to the total weight of the composition |
| --- | --- |
| Ivermectin | 1.00 |
| Brimonidine tartrate | 0.20 |
| EDTA | 0.1 |
| Polysorbate 80 | 8.0 |
| Propylene glycol | 20.00 |
| Benzyl alcohol | 3 |
| Water | qs 100 |

EXAMPLE 2

| Ingredients | % by weight relative to the total weight of the composition |
| --- | --- |
| Emamectin | 0.5 |
| Brimonidine tartrate | 0.3 |
| Codex petroleum jelly | 56.00 |
| Liquid petroleum jelly | 43.00 |

EXAMPLE 3

| Ingredients | % by weight relative to the total weight of the composition |
| --- | --- |
| Ivermectin | 1.40 |
| Oxymetazoline hydrochloride | 0.20 |
| Glycerol | 4.0 |
| Steareth-2 | 1.0 |
| Steareth-21 | 2.0 |
| Aluminum magnesium silicate/titanium dioxide/silica | 1.0 |
| Methyl para-hydroxybenzoate | 0.2 |
| Propyl para-hydroxybenzoate | 0.1 |
| Disodium EDTA | 0.05 |
| Citric acid monohydrate | 0.05 |
| Isopropyl palmitate | 4.0 |
| Glyceryl/PEG 100 stearate | 2.0 |
| Self-emulsifiable wax | 1.0 |
| Palmitostearic acid | 2.00 |
| Dimethicone 200-350 cS | 0.5 |
| Propylene glycol | 4.0 |
| Glyceryl triacetate | 1.00 |
| Phenoxyethanol | 0.5 |
| 10% sodium hydroxide | qs pH |
| Water | qs 100 |

EXAMPLE 4

| Ingredients | % by weight relative to the total weight of the composition |
| --- | --- |
| Ivermectin | 0.03 |
| Brimonidine | 0.15 |
| Polysorbate 80 | 2.00 |
| Benzalkonium chloride | 0.05 |
| EDTA | 0.05 |
| Water | qs 100 |
| Buffer system | pH 6.3 |

EXAMPLE 5

Evaluation of the Anti-Inflammatory Activity of Ivermectin and of Brimonidine after a Single Topical Application in the Arachidonic Acid-Induced Mouse Ear Edema Test on Balb/c Mice Arachidonic acid is dissolved in a mixture of THF/methanol at 4%.

Treatment:

Ivermectin is dissolved in the solution of arachidonic acid (AA) and tested at the concentration of 1%.

20 µl of the solution are applied to the internal surface of the right ear.

The thickness of the ear is measured at T+1 h, T+2 h and T+4 h.

Results:

FIG. 1 represents the average measurement of the thickness of the ear edema, i.e. the average measurement of the thickness of the ear after treatment, from which is subtracted the average measurement of the thickness of the ear obtained with the control (nontreated) group, this being after treatment with 4% arachidonic acid (▨), 1% ivermectin (□), 0.2% brimonidine (▰), and the combination of ivermectin and brimonidine (▨).

Indomethacin (positive control) at 5% inhibits the ear edema caused by arachidonic acid by 95% (***).

Ivermectin alone (1%) reduces the ear edema by 56% (**).

The combination of ivermectin (1%) with brimonidine (0.2%) inhibits the ear edema caused by arachidonic acid by 84% (***); it therefore shows a strong anti-inflammatory effect in the arachidonic acid-induced mouse ear edema model.

EXAMPLE 6

Evaluation of the Anti-Inflammatory Activity of Ivermectin and of Brimonidine after a Single Topical Application in the TPA-Induced Mouse Ear Edema Test on Balb/c Mice Treatment:

The edema is induced by means of a single application of 20 µl of TPA (phorbol 12-myristate 13-acetate) dissolved in ethanol at 0.01%.

The test compounds are diluted in the TPA solution.

A positive control, β-methasone valerate (BMV) at 0.01% is also tested; it inhibits the mouse ear edema by 89%.

Ivermectin is applied at a concentration of 0.1%, 0.3% and 1%. Brimonidine is added at the concentration of 0.2%.

The thickness of the mouse ear is measured at T+6 h.

Figure 2:
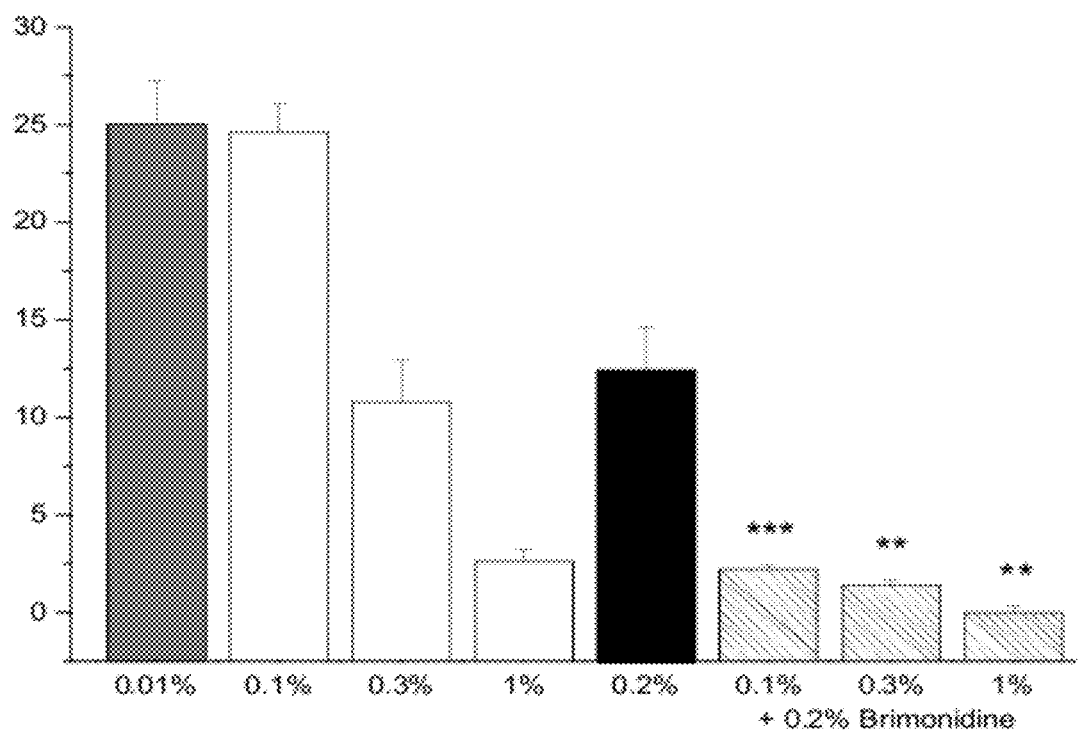
FIG. 2 is a bar graph of the average measurement of the thickness of the mouse ear after various treatments as detailed later herein, as a function of the dose of the test compound(s).

Results:

The results are presented in FIG. 2.

FIG. 2 represents the average measurement of the ear edema thickness as a function of the dose of test compound as %, i.e. the average measurement of the ear thickness after treatment, from which is subtracted the average measurement of the thickness of the ear obtained with the control (non-treated) group, this being after treatment with TPA at 0.01% (■),
ivermectin at respectively 0.1, 0.3 and 1% (□),
brimonidine at 0.2% (■).

the combination of ivermectin and brimonidine (▨)

After a single topical application of ivermectin at 0.3% and 1% diluted in the TPA solution, a reduction in the ear edema of respectively 57% () and 90% (*) is observed.

The application of brimonidine alone at 0.2% reduces the mouse ear edema by 50%.

The combination of ivermectin (at 0.1, 0.3 and 1%) and brimonidine (0.2%) has a dose-dependent anti-inflammatory effect, and reduces the TPA-induced ear edema by, respectively, 91% (*) (at 0.1%), 94% (*) (at 0.3%) and 100% (***) (at 1%).

The invention claimed is:

1. A pharmaceutical composition comprising, in a physiologically acceptable medium, ivermectin in an amount of from 0.01% to 5% by weight of the composition and brimonidine or a salt thereof in an amount of from 0.01% to 5% by weight of the composition.

2. A pharmaceutical composition comprising, in a physiologically acceptable medium, ivermectin in an amount of from 0.01% to 5% by weight of the composition and brimonidine or brimonidine tartrate in an amount of from 0.01% to 5% by weight of the composition.

3. A pharmaceutical composition comprising, in a physiologically acceptable medium, ivermectin in an amount of 0.1%, 0.3% or 1% by weight of the composition and brimonidine in an amount of 0.2% by weight of the composition.

4. The pharmaceutical composition as claimed in claim 1, wherein ivermectin is present in an amount of 0.1%, 0.3% or 1% by weight of the composition.

5. The pharmaceutical composition as claimed in claim 2, wherein ivermectin is present in an amount of 0.1%, 0.3% or 1% by weight of the composition.

6. A method for treating rosacea, the method comprising topically administering to a subject in need of such treatment, a pharmaceutical composition as claimed in claim 1.

7. A method for treating rosacea, the method comprising topically administering to a subject in need of such treatment, a pharmaceutical composition as claimed in claim 2.

8. A method for treating rosacea, the method comprising topically administering to a subject in need of such treatment, a pharmaceutical composition as claimed in claim 3.

9. A method for treating rosacea, the method comprising topically administering to a subject in need of such treatment, a pharmaceutical composition as claimed in claim 4.

10. A method for treating rosacea, the method comprising topically administering to a subject in need of such treatment, a pharmaceutical composition as claimed in claim 5.

* * * * *